(12) United States Patent
Kwon

(10) Patent No.: US 12,376,789 B2
(45) Date of Patent: Aug. 5, 2025

(54) METHOD OF PROVIDING DIAGNOSTIC INFORMATION ON ALZHEIMER'S DISEASE USING BRAIN NETWORK

(71) Applicant: Industry-Academic Cooperation Foundation Chosun University, Gwangju (KR)

(72) Inventor: Goo-Rak Kwon, Gwangju (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 466 days.

(21) Appl. No.: 17/592,744

(22) Filed: Feb. 4, 2022

(65) Prior Publication Data
US 2023/0148955 A1    May 18, 2023

(30) Foreign Application Priority Data
Nov. 12, 2021   (KR) .................. 10-2021-0155359

(51) Int. Cl.
*A61B 5/00*    (2006.01)
*G06T 7/00*    (2017.01)
*G16H 50/20*   (2018.01)

(52) U.S. Cl.
CPC .......... *A61B 5/4842* (2013.01); *A61B 5/4088* (2013.01); *A61B 5/7264* (2013.01); *G06T 7/0012* (2013.01); *G16H 50/20* (2018.01); *G06T 2207/10088* (2013.01); *G06T 2207/10104* (2013.01); *G06T 2207/10108* (2013.01); *G06T 2207/20072* (2013.01); *G06T 2207/20081* (2013.01); *G06T 2207/30016* (2013.01)

(58) Field of Classification Search
CPC ..... A61B 5/4842; A61B 5/4088; A61B 5/055; A61B 6/032; G06T 7/0012; G06T 2207/20072; G06T 2207/30016; G06T 2207/10088; G06T 2207/10104; G06T 2207/10108; G16H 50/20
See application file for complete search history.

(56) References Cited

FOREIGN PATENT DOCUMENTS

| KR | 10-2021-0067592 | 6/2021 |
| KR | 10-2021-0082617 | 7/2021 |

OTHER PUBLICATIONS

Susan S. Spencer, William H. Theodore, Samuel F. Berkovic, Clinical applications: MRI, SPECT, and PET, MRI, vol. 13, Issue 8, 1995, pp. 1119-1124, ISSN 0730-725X, https://doi.org/10.1016/0730-725X(95)02021-K. (Year: 1995).*

Aditya Grover and Jure Leskovec. 2016. Node2vec: Scalable Feature Learning for Networks. In Proceedings of the 22nd ACM SIGKDD International Conference on Knowledge Discovery and Data Mining (KDD '16). Ass. for Computing Machinery, New York, NY, USA, 855-864. https://doi.org/10.1145/2939672.2939754 (Year: 2016).*

(Continued)

*Primary Examiner* — Stephen R Koziol
*Assistant Examiner* — Ashley L. Hytrek
(74) *Attorney, Agent, or Firm* — LEX IP MEISTER, PLLC

(57) ABSTRACT

The present invention relates to a method of providing diagnostic information for Alzheimer's disease using a brain network.

4 Claims, 14 Drawing Sheets

(56) References Cited

OTHER PUBLICATIONS

Hojjati SH, Ebrahimzadeh A, Babajani-Feremi A. Identification of the Early Stage of Alzheimer's Disease Using Structural MRI and Resting-State fMRI. Front Neurol. Aug. 30, 2019;10:904. doi: 10.3389/fneur.2019.00904. PMID: 31543860; PMCID: PMC6730495. (Year: 2019).*

Deepak Ranjan Nayak, Ratnakar Dash, Banshidhar Majhi, Yudong Zhang, A hybrid regularized extreme learning machine for automated detection of pathological brain, Biocybernetics and Biomedical Eng., vol. 39, Iss. 3, 2019, pp. 880-892, ISSN 0208-5216, https://doi.org/10.1016/j.bbe.2019.08.005. (Year: 2019).*

Matlab. (May 3, 2020). Feature selection library. MathWorks—Maker of Matlab and Simulink—Matlab & Simulink. https://www.mathworks.com/matlabcentral/fileexchange/56937-feature-selection-library#version_history_tab (Year: 2020).*

Ma, J., Zhu, X., Yang, D., Chen, J., Wu, G. (2020). Attention-Guided Deep Graph Neural Network for Longitudinal Alzheimer's Disease Analysis. In: Martel, A.L., et al. MICCAI 2020. MICCAI 2020. Lecture Notes in Computer Science(), vol. 12267. Springer, Cham. https://doi.org/10.1007/978-3-030-59728-3_38 (Year: 2020).*

Song, X., Frangi, A., Xiao, X., Cao, J., Wang, T., Lei, B. (2020). Integrating Similarity Awareness and Adaptive Calibration in GCN to Predict Disease. In: Martel, A.L., et al. MICCAI 2020. Lecture Notes in Computer Science(), vol 12267. Springer, Cham. https://doi.or (Year: 2020).*

Lama RK, Kwon GR. Diagnosis of Alzheimer's Disease Using Brain Network. Front Neurosci. Feb. 5, 2021;15:605115. doi: 10.3389/fnins.2021.605115. PMID: 33613178; PMCID: PMC7894198. (Year: 2021).*

M. Xu, D. L. Sanz, P. Garces, F. Maestu, Q. Li and D. Pantazis, "A Graph Gaussian Embedding Method for Predicting Alzheimer's Disease Progression With MEG Brain Networks," in IEEE Transactions on Biomedical Engineering, vol. 68, No. 5, pp. 1579-1588, May 2021, doi: 10.1109/TBME.2021.3049199. (Year: 2021).*

Ramesh Kumar Lama et al., "Diagnosis of Alzheimer's Disease Using Brain Network", Frontiers in Neuroscience, Feb. 5, 2021, doi: 10.3389/fnins.2021.605115.

* cited by examiner

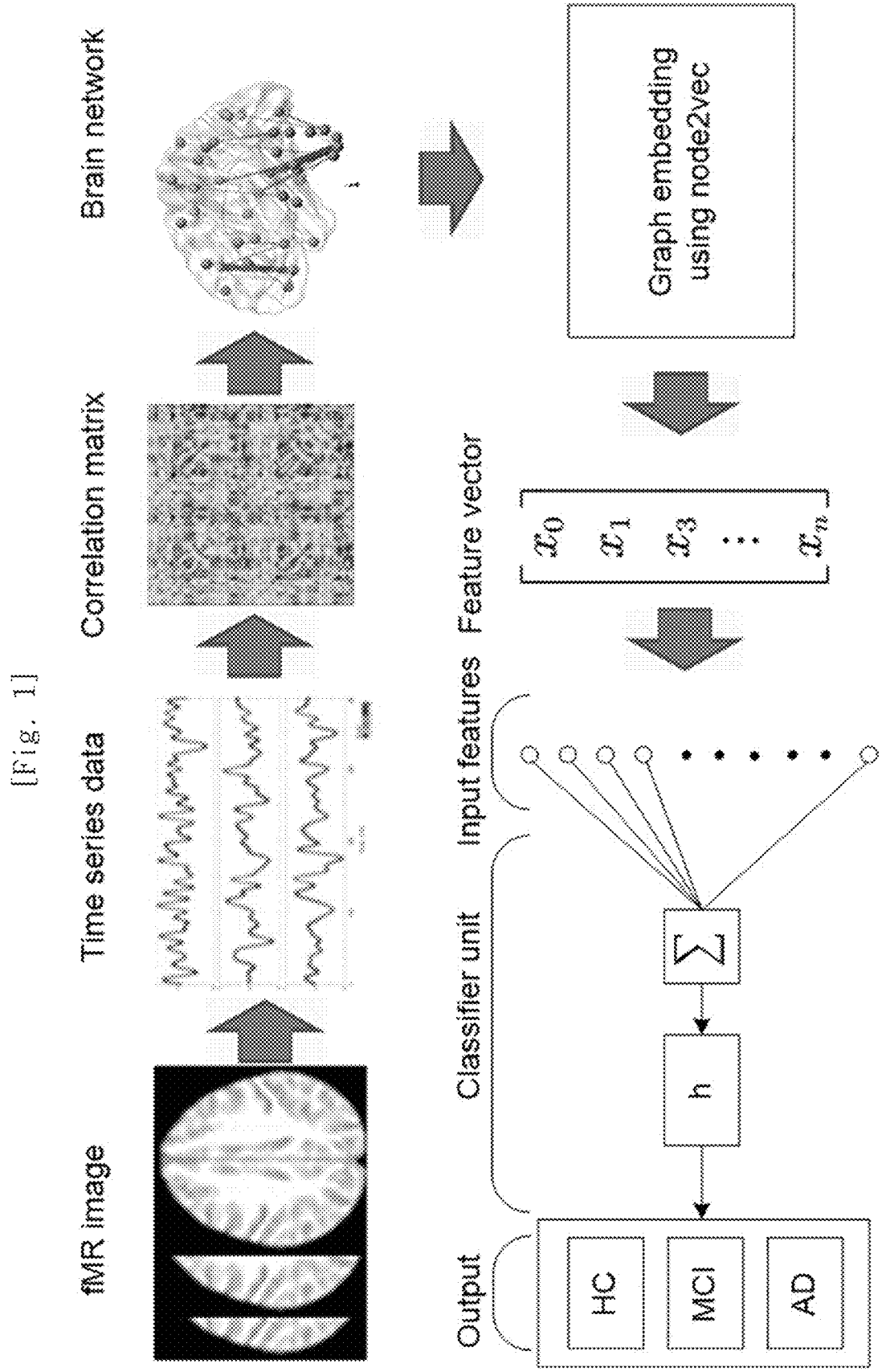
[Fig. 1]

[Fig. 2]
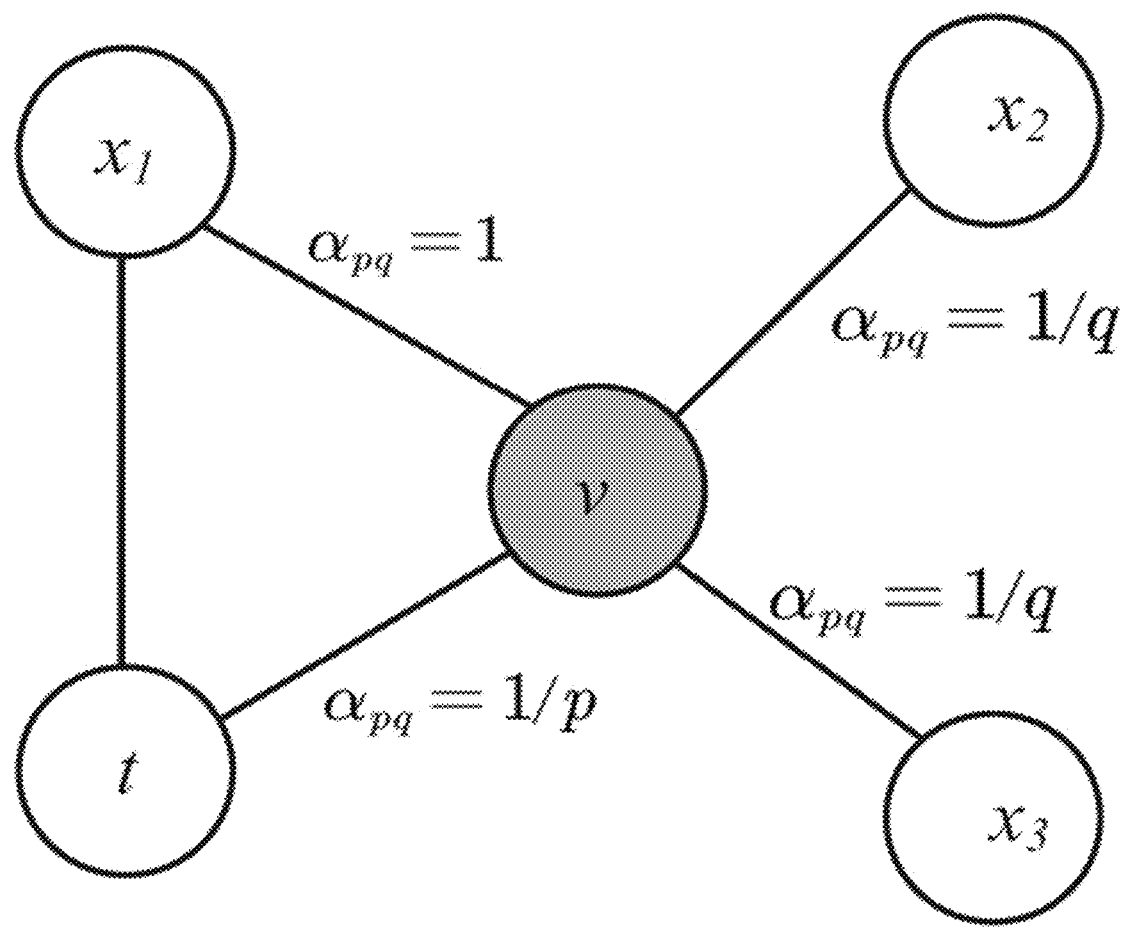

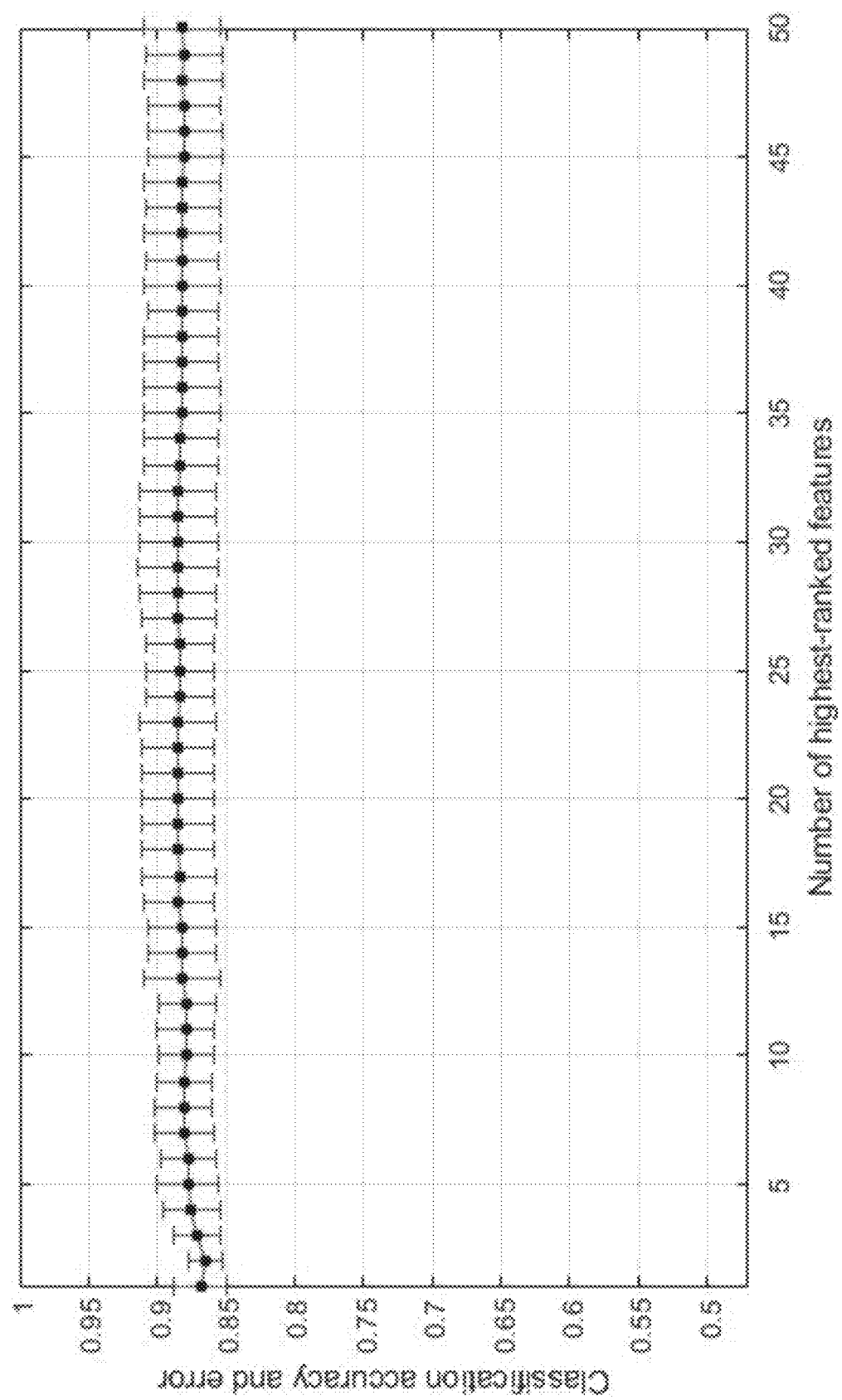
[Fig. 3]

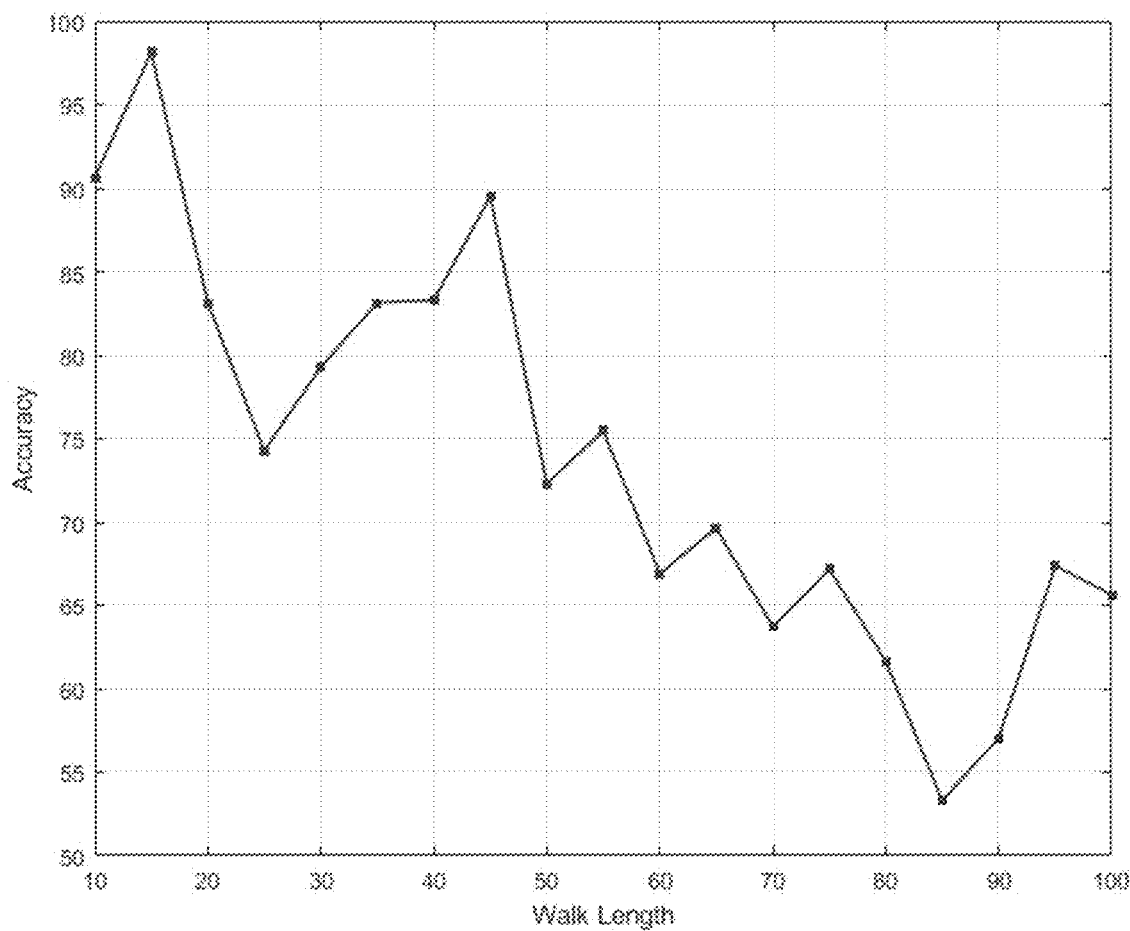
[Fig. 4(A)]

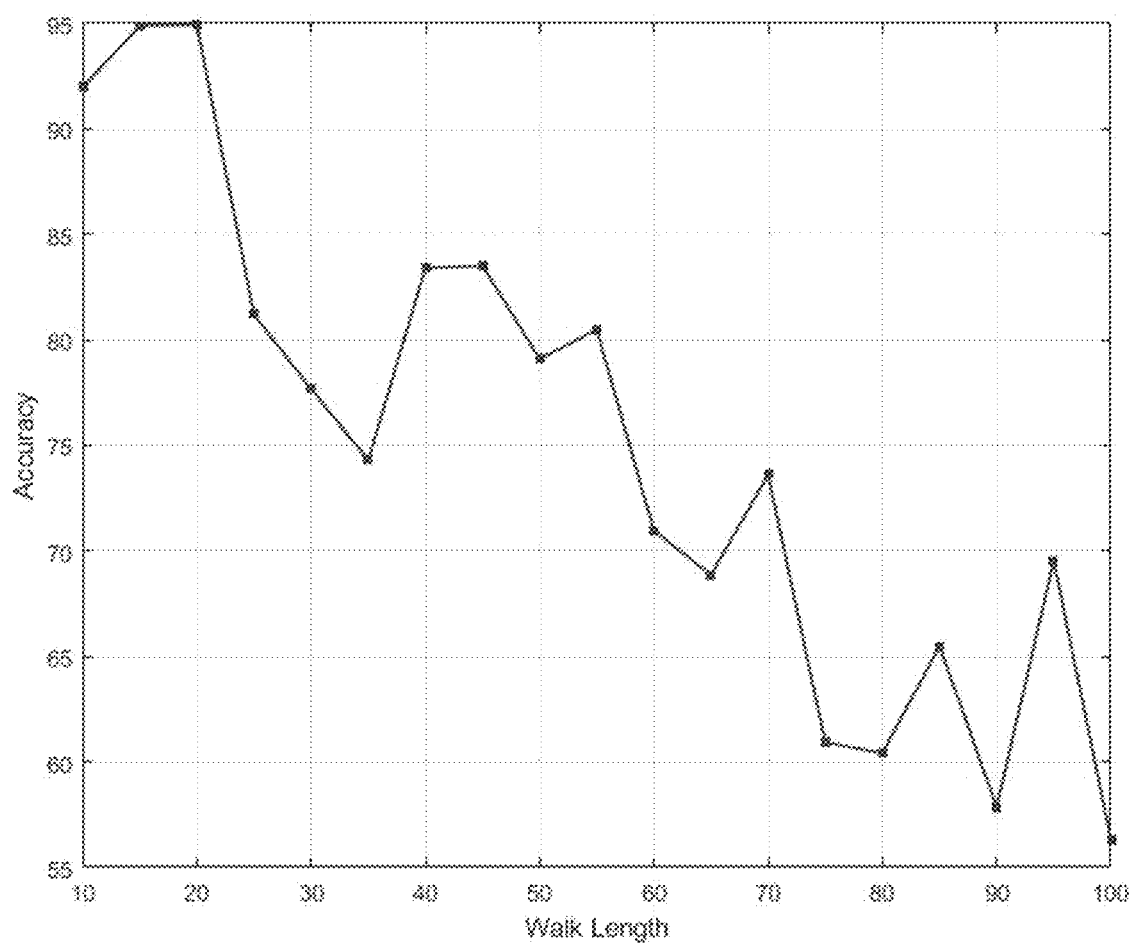
[Fig. 4(B)]

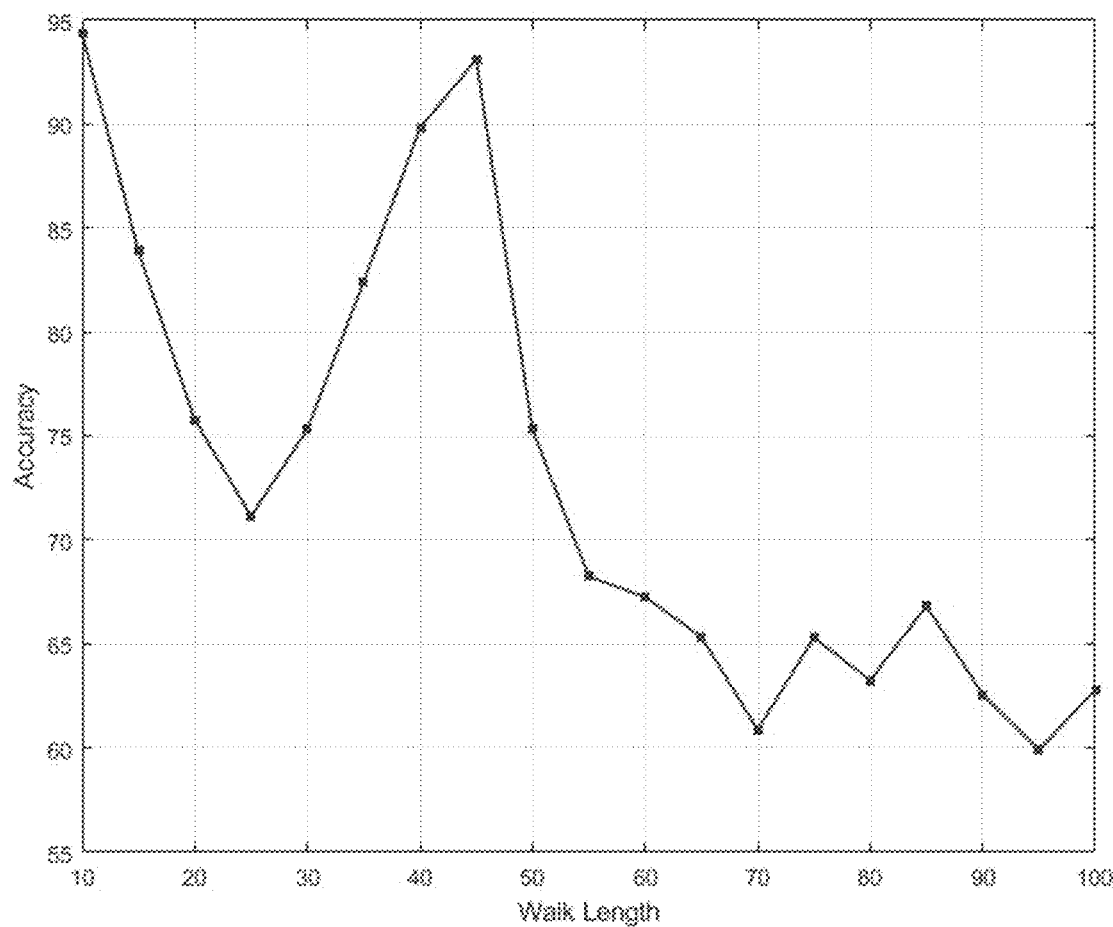
[Fig. 4(C)]

[Fig. 5]

| Feature selection method | Performance metrics | Mean (%) | Standard deviation | Max (%) | Min (%) |
|---|---|---|---|---|---|
| LASSO | Accuracy | 87.723 | 0.468 | 88.663 | 85.82 |
| | Sensitivity | 90.93 | 0.341 | 91.525 | 89.50 |
| | Specificity | 84.52 | 0.792 | 85.891 | 82.14 |
| | F-measure | 0.883 | | | |
| FSASL | Accuracy | 76.181 | 1.069 | 78.551 | 73.45 |
| | Sensitivity | 76.233 | 1.255 | 78.839 | 72.58 |
| | Specificity | 75.664 | 1.264 | 77.868 | 72.20 |
| | F-measure | 0.785 | | | |
| LLCFS | Accuracy | 75.737 | 1.004 | 78.690 | 71.64 |
| | Sensitivity | 74.205 | 1.069 | 77.031 | 70.11 |
| | Specificity | 77.881 | 1.378 | 81.036 | 73.64 |
| | F-measure | 0.817 | | | |
| CFS | Accuracy | 80.517 | 1.737 | 82.86 | 74.005 |
| | Sensitivity | 80.035 | 1.813 | 82.22 | 73.25 |
| | Specificity | 79.16 | 1.977 | 81.79 | 73.064 |
| | F-measure | 0.867 | | | |
| SVM-RFE | Accuracy | 68.57 | 1.186 | 70.474 | 65.60 |
| | Sensitivity | 75.99 | 1.676 | 78.832 | 71.715 |
| | Specificity | 60.92 | 1.301 | 63.426 | 57.34 |
| | F-measure | 0.6743 | | | |

[Fig. 6]

| Feature selection method | Performance metrics | Mean (%) | Standard deviation | Max (%) | Min (%) |
|---|---|---|---|---|---|
| LASSO | Accuracy | 96.11 | 0.859 | 96.88 | 91.33 |
|  | Sensitivity | 95.03 | 1.080 | 95.93 | 89.84 |
|  | Specificity | 97.18 | 0.798 | 97.84 | 92.93 |
|  | F-measure | 0.973 | | | |
| FSASL | Accuracy | 85.85 | 0.9129 | 87.503 | 80.88 |
|  | Sensitivity | 79.27 | 0.986 | 81.484 | 76.01 |
|  | Specificity | 92.03 | 1.4433 | 93.308 | 85.40 |
|  | F-measure | 0.937 | | | |
| LLCFS | Accuracy | 82.29 | 0.624 | 83.39 | 80.77 |
|  | Sensitivity | 77.54 | 0.73 | 78.566 | 75.408 |
|  | Specificity | 86.81 | 1.081 | 88.41 | 83.74 |
|  | F-measure | 0.85 | | | |
| CFS | Accuracy | 80.67 | 1.68 | 90.427 | 74.48 |
|  | Sensitivity | 88.43 | 2.328 | 74.968 | 80.49 |
|  | Specificity | 72.38 | 1.3677 | 74.486 | 68.58 |
|  | F-measure | 0.795 | | | |
| SVM-RFE | Accuracy | 80.20 | 0.920 | 82.001 | 77.89 |
|  | Sensitivity | 84.00 | 1.207 | 85.99 | 79.86 |
|  | Specificity | 75.91 | 1.251 | 77.806 | 73.29 |
|  | F-measure | 0.815 | | | |

[Fig. 7]

| Feature selection method | Performance metrics | Mean (%) | Standard deviation | Max (%) | Min (%) |
|---|---|---|---|---|---|
| LASSO | Accuracy | 93.86 | 0.766 | 94.90 | 89.128 |
|  | Sensitivity | 91.93 | 0.757 | 93.67 | 89.836 |
|  | Specificity | 95.92 | 1.204 | 96.61 | 88.580 |
|  | F-measure | 0.968 | | | |
| FSASL | Accuracy | 85.358 | 1.030 | 86.76 | 80.29 |
|  | Sensitivity | 85.088 | 0.951 | 86.61 | 80.47 |
|  | Specificity | 85.201 | 1.4227 | 86.829 | 79.27 |
|  | F-measure | 0.879 | | | |
| LLCFS | Accuracy | 90.32 | 1.06316 | 91.88 | 86.50 |
|  | Sensitivity | 93.33 | 2.0782 | 95.63 | 87.43 |
|  | Specificity | 87.49 | 0.9471 | 89.56 | 85.75 |
|  | F-measure | 0.895 | | | |
| CFS | Accuracy | 79.13 | 1.2768 | 81.595 | 75.10 |
|  | Sensitivity | 83.59 | 1.2281 | 85.60 | 78.94 |
|  | Specificity | 74.83 | 1.7084 | 78.927 | 70.54 |
|  | F-measure | 0.795 | | | |
| SVMRFE | Accuracy | 77.5974 | 0.8177 | 78.93 | 74.98 |
|  | Sensitivity | 76.802 | 1.1299 | 79.225 | 73.26 |
|  | Specificity | 78.182 | 0.8359 | 79.289 | 75.44 |
|  | F-measure | 0.8169 | | | |

[Fig. 8]

| Feature selection method | Performance metrics | Mean (%) | Standard deviation | Max (%) | Min (%) |
|---|---|---|---|---|---|
| LASSO | Accuracy | 90.63 | 0.515 | 91.51 | 88.52 |
|  | Sensitivity | 87.044 | 0.585 | 88.03 | 85.44 |
|  | Specificity | 94.315 | 0.671 | 95.35 | 90.95 |
|  | F-measure |  | 0.958 |  |  |
| FSASL | Accuracy | 82.895 | 1.4020 | 85.60 | 80.19 |
|  | Sensitivity | 78.206 | 1.5118 | 81.99 | 75.21 |
|  | Specificity | 87.712 | 1.7666 | 90.02 | 82.85 |
|  | F-measure |  | 0.8360 |  |  |
| LLCFS | Accuracy | 81.19 | 1.438 | 83.37 | 77.68 |
|  | Sensitivity | 85.15 | 2.087 | 88.068 | 80.49 |
|  | Specificity | 76.39 | 1.25 | 78.983 | 73.65 |
|  | F-measure |  | 0.8095 |  |  |
| CFS | Accuracy | 88.37 | 1.78 | 91.18 | 83.25 |
|  | Sensitivity | 87.95 | 1.72 | 91.98 | 84.52 |
|  | Specificity | 88.79 | 2.17 | 90.71 | 81.28 |
|  | F-measure |  | 0.903 |  |  |
| SVMRFE | Accuracy | 65.99 | 1.48 | 68.51 | 62.05 |
|  | Sensitivity | 65.03 | 1.41 | 67.73 | 61.46 |
|  | Specificity | 67.40 | 2.327 | 70.53 | 61.27 |
|  | F-measure |  | 0.671 |  |  |

[Fig. 9]

| Feature selection method | Performance metrics | Mean (%) | Standard deviation | Max (%) | Min (%) |
|---|---|---|---|---|---|
| LASSO | Accuracy | 98.91 | 0.456 | 99.25 | 95.82 |
|  | Sensitivity | 99.68 | 0.56 | 100.0 | 95.48 |
|  | Specificity | 98.11 | 0.46 | 98.51 | 96.00 |
|  | F-measure | | 0.9856 | | |
| FSASL | Accuracy | 81.28 | 1.010 | 83.01 | 77.64 |
|  | Sensitivity | 84.61 | 1.389 | 86.62 | 79.81 |
|  | Specificity | 77.92 | 1.121 | 79.81 | 73.038 |
|  | F-measure | | 0.833 | | |
| LLCFS | Accuracy | 76.27 | 0.631 | 78.31 | 74.70 |
|  | Sensitivity | 71.08 | 1.388 | 75.37 | 68.23 |
|  | Specificity | 81.40 | 1.005 | 82.69 | 76.80 |
|  | F-measure | | 0.800 | | |
| CFS | Accuracy | 86.16 | 2.25 | 88.96 | 80.47 |
|  | Sensitivity | 92.28 | 2.33 | 95.11 | 86.14 |
|  | Specificity | 79.72 | 2.376 | 82.75 | 73.88 |
|  | F-measure | | 0.8517 | | |
| SVMRFE | Accuracy | 71.92 | 0.832 | 74.43 | 69.93 |
|  | Sensitivity | 66.90 | 1.493 | 71.14 | 63.53 |
|  | Specificity | 76.68 | 1.187 | 79.61 | 72.88 |
|  | F-measure | | 0.7762 | | |

[Fig. 10]

| Feature selection method | Performance metrics | Mean (%) | Standard deviation | Max (%) | Min (%) |
|---|---|---|---|---|---|
| LASSO | Accuracy | 97.80 | 0.9862 | 98.32 | 91.99 |
| | Sensitivity | 97.62 | 1.0065 | 97.92 | 91.73 |
| | Specificity | 97.74 | 1.0720 | 98.5 | 92.07 |
| | F-measure | | 0.98 | | |
| FSASL | Accuracy | 83.71 | 0.90 | 85.00 | 78.15 |
| | Sensitivity | 90.63 | 1.57 | 92.23 | 84.12 |
| | Specificity | 77.10 | 1.098 | 79.74 | 72.55 |
| | F-measure | | 0.838 | | |
| LLCFS | Accuracy | 90.04 | 1.43 | 92.02 | 86.07 |
| | Sensitivity | 90.23 | 1.43 | 91.94 | 86.74 |
| | Specificity | 90.09 | 1.77 | 92.52 | 84.62 |
| | F-measure | | 0.903 | | |
| CFS | Accuracy | 84.41 | 1.95 | 86.81 | 79.18 |
| | Sensitivity | 90.37 | 2.14 | 93.26 | 83.73 |
| | Specificity | 78.10 | 1.90 | 80.79 | 72.84 |
| | F-measure | | 0.83 | | |
| SVMRFE | Accuracy | 82.87 | 0.903 | 83.96 | 78.832 |
| | Sensitivity | 81.68 | 1.22 | 84.34 | 77.10 |
| | Specificity | 84.11 | 0.94 | 85.21 | 80.72 |
| | F-measure | | 0.854 | | |

[Fig. 11]

| Dataset | Feature measures | Classifier | Accuracy (%) | Reference |
|---|---|---|---|---|
| AD:77, HC: 173 | Combination of FC matrices, FC dynamics, ALFF | AUC | 85 | de Vos et al., 2018 |
| AD: 12, HC: 12 | Difference between DMN and SN map | LDA | 92 | Zhou et al., 2010 |
| AD: 34, HC: 45 | Graph measures | Naïve Bayes | 93.3 | Khazaee et al., 2017 |
| AD: 15, HC: 16 | Averaged voxel intensities of core regions in resting state networks: DMN, DAN, VAN | Multivariate ROC | 95 | Wu et al., 2018 |

[Fig. 12]

| Dataset | Feature measures | Classifier | Accuracy (%) | References |
|---|---|---|---|---|
| MCI: 31, HC: 31 | Functional activity co-variations of ROIs | SVM | 62.90 | Eavani et al., 2013 |
| MCI: 31, HC: 31 | Group sparse representation | SVM | 66.13 | Wee et al., 2014 |
| MCI: 31, HC: 31 | SDFN | SVM | 70.97 | Leonardi et al., 2013 |
| MCI: 31, HC: 31 | Deep auto encoder and HMM | SVM | 72.58 | Suk et al., 2016 |

METHOD OF PROVIDING DIAGNOSTIC INFORMATION ON ALZHEIMER'S DISEASE USING BRAIN NETWORK

TECHNICAL FIELD

The present invention relates to providing method of diagnostic information on Alzheimer's disease using brain network.

BACKGROUND ART

Alzheimer's disease (AD), which causes majority of dementia is a progressive neurodegenerative disease. The subtle neuropathological process of AD begins years before the visible, progressive cognitive impairment that make it difficult to remember and learn new information. Currently there is no cure and treatment to slow or stop its progression. Currently, more research works are focused toward earlier intervention of AD. Thus, accurate diagnosis of disease at its early stage is critical.

Advances in neuroimaging technology are enabling early and accurate detection of AD. The study of progression of disease and early detection is carried out by using different imaging models, such as electroencephalography (EEG), functional magnetic resonance imaging (fMRI), single-photon emission computed tomography (SPECT) and positron emission tomography (PET).

Similarly, structural magnetic resonance imaging (MRI) is the most commonly used imaging system for study of AD. The feature extracted from MRI is typically gray matter volumes and measured as important biomarker for the study of neurodegeneration, alterations of hippocampal white matter pathways is often observed in AD. Several studies reveal the alterations in widely distributed functional and structural connectivity pairs are prevalent in AD and mild cognitive impairment (MCI). Additionally, in recent studies, the resting-state functional magnetic resonance imaging (rs-fMRI) has been widely used for the investigations of progression of AD. This imaging system evaluates the impulsive variabilities seen in the blood oxygenation level-dependent (BOLD) indications in various regions of the brain. Several studies are carried out based on aberrant regional spontaneous fluctuation of BOLD, functional connectivity and alteration in functional brain network. These studies are carried out in different networks, such as default mode network, somatomotor network, dorsal attention network, limbic network, and frontoparietal control network. Thus, the graph theory based network analyses of human brain functional connectomes, provides better insights of the network structure to reveal abnormal patterns of organization of functional connectivity in AD infected brain.

Graph theory is a mathematical approach to study complex networks. Network is constructed of vertices which are interconnected by edges. Vertices in our case are brain regions. Graph theory is widely used as tool for identifying anatomically localized subnetworks associated with neuronal alterations in different neurodegenerative diseases. In fMRI images, graph represents causal relations or correlations of different nodes in constructed networks. However, the brain network built by graph has non-Euclidian characteristics. Thus, applying machine learning techniques to analyze the brain networks is challenging. We use graph embedding to transform graphs to a vector or set of vectors to overcome this problem. Embedding captures the graph topology, vertex-vertex relationship, and other relevant graph information. In the current study, we used node2vec graph embedding technique to transform vertex and edge of brain network graph to feature vector. With the help of this model we have analyzed and classified the networks of brain from fMRI data into AD, MCI, and HC.

Recent studies suggest the brain functional connectivity impairment is the early event occurred in case of Alzheimer's disease (AD) as well as mild cognitive impairment (MCI). We model the brain as a graph based network to study these impairments. In this paper, we present a new diagnosis approach using graph theory based features from functional magnetic resonance (fMR) images to discriminate AD, MCI, and healthy control (HC) subjects using different classification techniques. These techniques include linear support vector machine (LSVM), and regularized extreme learning machine (RELM). We used pairwise Pearson's correlation-based functional connectivity to construct the brain network. We compare the classification performance of brain network using Alzheimer's disease neuroimaging initiative (ADNI) datasets. Node2vec graph embedding approach is employed to convert graph features to feature vectors. Experimental results show that the SVM with LASSO feature selection method generates better classification accuracy compared to other classification technique.

PRIOR ART

Patent

1. Korean Patent Registration No. 2021-0067592
2. Korean Patent Registration No. 2021-0082617

DETAILED DESCRIPTION OF THE INVENTION

Summary

An object of the present invention is to provide a method of providing diagnostic information for classifying Alzheimer's disease or mild cognitive impairment from normal people using fMRI feature-based graph theory.

Technical Problem

The present invention provides a method of providing diagnostic information for classifying Alzheimer's disease progression, including; 1) extracting a feature; 2) constructing a brain network using graph theory; 3) converting the graph to a feature vector using node2vec graph embedding; 4) selecting a feature; 5) classifying Alzheimer's disease progression; and 6) evaluating the classification result.

According to an embodiment of the present invention, wherein the feature is extracted from one selected from the group consisting of electroencephalography (EEG), functional magnetic resonance imaging (fMRI), single-photon emission computed tomography (SPECT) and positron emission tomography (PET).

According to another embodiment of the present invention, wherein the graph embedding includes sampling, skip-gram, and computing embedding.

According to other embodiment of the present invention, wherein the selection is selected from the group consisting of support vector machine-recursive feature elimination (SVM-RFE), least absolute shrinkage and selection operator (LASSO), feature selection with adaptive structure learning (FSASL), local learning and clustering based feature selection (LLCFS) and pairwise correlation based feature selection (CFS).

According to an embodiment of the present invention, wherein the evaluation is verified with one or more selected from the group consisting of accuracy (ACC), sensitivity (SEN), and specificity (SPE).

According to another embodiment of the present invention, wherein the classification uses one or more selected from the group consisting of regularized extreme learning machine (RELM) and linear support vector machine (LSVM).

According to other embodiment of the present invention, wherein the Alzheimer's disease progression is one selected from the group consisting of healthy control, mild cognitive impairment and Alzheimer's disease.

Technical Solution

The method of providing diagnostic information for classifying Alzheimer's disease or mild cognitive impairment according to the present invention has an effect of providing an optimal diagnostic means capable of early diagnosis to grasp the patient's condition.

BRIEF DESCRIPTION OF THE DRAWINGS

FIG. 1. Block diagram of the proposed diagnosis system.

FIG. 2. Illustration of node selection in node2vec algorithm.

FIG. 3. Average accuracy and standard deviation for AD against HC using RELM classification method on reduced datasets using LASSO feature selection.

FIGS. 4(A) to 4(C). The effect of different parameter values of Walk Length of Node2vec on performance (A) AD against HC, (B) HC against MCI, (C) AD against MCI.

FIG. 5. 10-fold cross-validation binary mean classification performance for AD against HC using RELM classifier using different feature selection methods.

FIG. 6. 10-fold cross-validation binary mean classification performance for HC against MCI using RELM classifier using different feature selection methods.

FIG. 7. 10-fold cross-validation binary mean classification performance for MCI against AD using RELM classifier using different feature selection methods.

FIG. 8. 10-fold cross-validation binary mean classification performance for AD against HC using LSVM classifier using different feature selection methods.

FIG. 9. 10-fold cross-validation binary mean classification performance for HC against MCI using LSVM classifier using different feature selection methods.

FIG. 10. 10-fold cross-validation binary mean classification performance for MCI against AD using LSVM classifier using different feature selection methods.

FIG. 11. Comparison of performance of binary classification AD against HC with state of the art methods using rs-fMRI.

FIG. 12. Comparison of performance of binary classification MCI against HC with state of the art methods using rs-fMRI.

DETAILED DESCRIPTION

Hereinafter, the present invention will be described in more detail through examples. These examples are only for illustrating the present invention and should not be construed as limiting the scope of the present invention to these examples.

<Example 1> fMRI Dataset

In our study, we have used the dataset from Alzheimer's disease neuroimaging initiative database (ADNI). The ADNI database was launched in 2004. The database consists of subjects of age ranging from 55-90 years. The goal of ADNI is to study the progression of the disease using different biomarkers. This includes clinical measures and assesses of the structures and functions of brain for the course of different disease states.

All participants were scanned using 3.0-Telsa Philips Achieva scanners at different centers. Same scanning protocol were followed for all participants and the set parameters were ratio of Repetition Time (TR) to Echo Time (TE) i.e., TR/TE=3000/30 ms, 140 volumes, also voxel thickness as 3.3 mm, acquisition matrix size=64×64, 48 slices, flip angle=80° Similarly, 3D T1-weighted images were collected using MPRAGE sense2 sequences with acquisition type 3D, field strength=3 Tesla, flip angle 9.0 degree, pixel spacing X=1.0547000169754028 mm; Pixel Spacing Y=1.0547000169754028 nm, slice thickness=1.2000000476837158 mm; echo time (TE) 2.859 ms, inversion time (TI) 0.0 ms, repetition time (TR) 6.6764 ms and weighting T1. We selected subjects as specified in Table 1.

TABLE 1

| | Number of subjects Mean (SD) | | |
|---|---|---|---|
| | HC (n = 31) | MCI (n = 31) | AD (n = 31) |
| Age (years) | 73.9 ± 5.4 | 74.5 ± 5.0 | 72.7 ± 7.0 |
| Global CDR | 0.04 ± 0.13 | 0.5 ± 0.18 | 0.95 ± 0.30 |
| MMSE | 28.9 ± 1.65 | 27.5 ± 2.02 | 20.87 ± 3.6 |

<Example 2> Subjects

We selected 93 subjects from ADNI2 cohort. The purpose of ADNI2 is to examine how brain imaging and other biomarkers can be used to measure the progression of MCI and early AD. The ADNI selects and categorizes participants in specific group based on certain inclusion criteria. The criteria are well defined in https://www.nia.nih.gov/alzheimers/clinical-trials/alzheimers-diseaseneuroimaging-initiative-2-adni2. We selected the subjects according to availability of both MRI and fMRI data. Thus, the subjects with following demographic status as shown in Table 1 with following average age, clinical dementia rating (CDR) and mini-mental state estimation (MMSE) out of all available data in ADNI2 cohort were selected in our study.

1. 31 HC subjects: 14 males, 17 females; age±SD=73.9±5.4 years with the mini-mental state estimation (MMSE) score of 28.9±1.65 and the range was 24-30.
2. 31 MCI subjects: 17 males, 14 females; age±SD=74.5±5.0 with the MMSE score of 27.5±2.02, and range was 22-30.
3. 31 AD subjects: 13 males, 18 females; age±SD=72.7±7.0 with MMSE=20.87±3.6, and the range was 14-26.

<Example 3> Data Preprocessing

We used data processing subordinate for the resting state fMRI via DPARSF and the statistical parametric mapping platform via SPM8 aimed at the preprocessing of rs-fMRI data. All the images initially obtained from scanner were in the format of digital imaging and communications in medicine (DICOM). We converted these images to neuroimaging informatics technology initiative (NIfTI) file format. Signal standardization and participant's adaptation to the noise while scanning each participant are carried out by discarding the first 10 time points for each participant. Next, we preformed preprocessing operation through following steps:

For slice-timing correction last slice was referred reference slice. Friston 24-parameter model with 6 parameters of head motion, 6 parameters of head motion from the previous time point, and 12 corresponding squared items were employed for realignment for head movement compensation. Similarly, after the realignment, individual structural images (T1-weighted MPRAGE) were registered to the mean functional image. For the standardization of the rs-fMRI toward the original place was accomplished with the help of diffeomorphic anatomical registration through exponentiated lie algebra (DARTEL) (resampling voxel size=3 mm×3 mm×3 mm). A 6 mm full width at half-maximum (FWHM) Gaussian kernel spatial smoothing was employed for the smoothing. Next, we performed linear trend exclusion and also the temporal band pass filtering which ranges at (0.01 Hz<f<0.08 Hz) on the time series of each voxel. Finally, cerebrospinal as well as white matter signals along with six head-motion parameters were regressed out to reduce the effects of nuisance signals.

This proposed method consists of the following four major functional steps as shown in FIG. 1:
1. Construct a brain network using graph theory.
2. Convert graph to feature vector using node2vec graph embedding.
3. Reduce the features.
4. Perform the classification using regularized extreme learning machine (RELM) and linear support vector machine (LSVM).

<Example 4> Construction of Brain Networks

For the construction of network from fMR images, we first preprocessed the raw fMR data as described in data preprocessing section. Next, we used the automated anatomical labeling (AAL) atlas to identify the brain regions of interest (ROI). The whole image was divided in 116 regions with each hemisphere. Next, we calculate the average time series of each ROI for each subject by averaging their time series across the voxels within each ROI. For each subject, a matrix of 130 rows and 116 columns was obtained. In the matrix, every row denotes the time series conforming to a give ROI, while information of total regions at a definite time point are stored at each column. The mean time series of each brain region were obtained for each individual by averaging the time series within the region. For $L_i=(I_i(1), I_i(2), \ldots, I_i(n))$ and $L_j=(I_j(1), I_j(2), \ldots, I_j(n))$ are two n length time series of brain region i and j, the Pearson's correlation (PC) between them can be calculated as $$PC_{ij} = \frac{cov(L_i, L_j)}{\sigma_{L_i}\sigma_{L_j}} \quad \text{[Equation 1]}$$

Where $cov(L_i, L_j)$ is covariance of variables $L_i$ and $L_j$. Similarly, $\sigma_{L_i}$ and $\sigma_{L_j}$ are standard deviation of variables $L_i$ and $L_j$. This operation results into 116×116 correlation matrix which defines the relation amongst different regions of brain and matches to the functional connectivity network.

<Example 5> Graph-Embedding

Graphs are complex data structures, consisting a finite set of vertices and set of edges which connect a pair of nodes. One of the possible solutions to manipulate prevalent pattern recognition algorithms on graphs is embedding the graph into vector space. Indeed, graph embedding is a bridge between statistical pattern recognition and graph mining. We employ the node2vec algorithm as graph embedding tool in this study. The node2vec algorithm aims to learn a vectorial representation of nodes in a graph by optimizing a neighborhood preserving objective. It extends the previous node embedding algorithm Deepwalk and it is inspired from the state of art word embedding algorithm word2vec.

In word2vec, given a set of sentences also known as corpus, the model learns word embedding by analyzing the context of each word in the body. The word2vec uses the neural network with one hidden layer to transform words into embedding vectors. This neural network is known as Skip-gram. This network is trained to predict the neighboring word in the sentence. It accepts the word at the input and is optimized such that it predicts the neighboring words in a sentence with high probability.

node2vec applies the same embedding approach to train and predict the neighborhood of a node in graph. However, word is replaced by the node and the bag of nodes is used instead of corpus. The sampling is used to generate this bag of nodes from a graph. Generally, the graph embedding consists of three steps:
1) Sampling A graph is sampled with random walks. This random walk results in bag of nodes of neighborhood from sampling. The bag of nodes acts as a collection of contexts for each node in the network. The innovation of node2vec with respect to Deepwalk is the use of flexible biased random walks on the network. In Deepwalk, random walk is obtained by a uniform random sampling over the linked nodes, while node2vec combine two different strategies for the network exploration: depth-first search (DFS) and breadth-first-search (BFS). For current random walk position at node v and traversed position at previous step at node t and neighboring nodes $x_1$, $x_2$ and $x_3$, the sampling of next node x is determined by evaluating the unnormalized transition probabilities $\pi_{vx}$ on edge (t,v) with the static edge weight $w_{vx}$ as shown in FIG. 2. This unnormalized transition probability is estimated based on search bias $\alpha$ defined by two parameters p and q such that $\pi_{vx}=\alpha_{pq}(t,x)\cdot w_{vx}$ where.

$$\alpha_{pq}(t, x) = \begin{cases} \frac{1}{p}, & \text{if } d_{tx} = 0 \\ 1, & \text{if } d_{tx} = 1 \\ \frac{1}{q}, & \text{if } d_{tx} = 2 \end{cases} \quad \text{[Equation 2]}$$

Here $d_{tx}$ denotes the shortest path distance between nodes t and x.

The parameter p determines the likelihood of sampling the node t again during random walk. When the value of p is high revisit of the node possibility is low. Similarly the parameter q allows to different between local and global nodes. If q>1, the random walk has the likelihood of sampling the nodes around the node v is high.

2) Training Skip-Gram

The bag of nodes generated from the random walk is fed into the skip-gram network. Each node is represented by a one-hot vector and maximizes the probability for predicting neighbor nodes. The one-hot vector has size same as the size of the set of unique words used in the text corpus. For each node only one dimension is equal to one and remaining are zeros. The position of dimension having one in vector defines the individual node.

3) Computing Embedding

The output of the hidden layer of the network is taken as the embedding of the graph.

<Example 6> Feature Reduction Techniques

1) Support Vector Machine-Recursive Feature Elimination (SVM-RFE)

Support vector machine-recursive feature elimination is a multivariate feature reduction algorithm is based on wrapper model. This method is recursive and in each of iteration of the RFE, LSVM model is trained. This method starts by constructing a model on the complete set of features and computing the importance score for each feature. The least important features are removed and the model is rebuilt and the importance scores are again computed. This recursive procedure is continued until all the features are eliminated. Then, the features are ranked according to the order of elimination. A detailed description of SVM-RFE procedure presented in a previous paper (Guyon et al., 2002). In this work, after applying SVM-RFE, the most significant training features that make the most of cross-validated accurateness are kept to train the classifiers.

2) Least Absolute Shrinkage and Selection Operator (LASSO)

Least absolute shrinkage and selection operator is a powerful method which is used to remove insignificant features. Two major tasks of this method are regularization and feature selection. This method minimizes residual sum of squares of the model using ordinary least square regression (OLS) by placing a constraint on the sum of the absolute values of the model parameters. LASSO computes model coefficients $\beta$ by minimizing the following function:

$$RSS_{LASSO}(\beta_i, \beta_0) = \underset{\beta}{\operatorname{argmin}}\left[\sum_{i=1}^{n}(y_i - (\beta_i x_i + \beta_0))^2 + \alpha\sum_{j=1}^{k}|\beta_j|\right] \quad \text{[Equation 3]}$$

Where, $x_i$ is the graph embedded feature input data, a vector of k values at observation j, and n is the number of observations. $y_i$ is the response at observation i. $\alpha$ is a non-negative user defined regularization parameter. This parameter controls the strength of penalty. When $\alpha$ is sufficiently large then coefficients are forced to be zero which leads to produce few relevant features. If $\alpha$ approaches 0 the model becomes OLS with more relevant features.

3) Features Selection with Adaptive Structure Learning (FSASL)

Features selection with adaptive structure learning is an unsupervised method which performs data manifold learning and feature selection. This method first utilizes the adaptive structure of the data to construct the global learning and the local learning. Next, the significant features are selected by integrating both of them with $L_{2,1}$-norm regularizer. This method utilizes the sparse reconstruction coefficients to extract the global structure of data for global learning. In sparse representation, each data sample $x_i$ can be approximated as a linear combination of all the other samples, and the optimal sparse combination weight matrix.

For local learning, this method directly learns a Euclidean distance induced probabilistic neighborhood matrix.

$$\min_{W,S,P}(\|W^T X - W^T XS\|^2 + \alpha\|S\|_1) + \beta\sum_{i,j}^{n}(\|W^T x_i - W^T x_j\|^2 P_{ij} + \mu P_{ij}^2) + \gamma\|W\|_{21} \quad \text{[Equation 4]}$$

$$\text{s.t. } S_{ii} = 0, P1_n = 1_n, P \geq 0, W^T XX^T X = I$$

Where, $\alpha$ is used to balancing the sparsity and the reconstruction error, $\beta$ and $\gamma$ are regularization parameters for global and local structure learning in first and second group and the sparsity of feature selection matrix in the third group. Similarly, S is used to guide the search of relevant global feature and P defines the local neighborhood of data sample $x_i$.

4) Local Learning and Clustering Based Feature Selection (LLCFS)

LLCFS is clustering based feature selection method. This method learns the adaptive data structure with selected features by constructing the k-nearest neighbor graph in the weighted feature space. The joint clustering and feature weight learning is performed by solving the following problem.

$$\min_{Y,\{W^i,b^i\}_{i=1}^{n},z} \sum_{i=1}^{n}\sum_{c'=1}^{c}\left[\sum_{x_j \in N_{x_i}} \beta(Y_{ic'} - x_j^T W_{c'}^i - b_c^i)^2 + (W_{c'}^i)^T \text{diag}(z^{-1})W_{c'}^i\right] \quad \text{[Equation 5]}$$

$$\text{s.t. } 1_d^T z = 1, z \geq 0$$

Where z the feature weight vector and $N_{x_i}$ is the k-nearest neighbor of $x_i$ based on z weighted features.

5) Pairwise Correlation Based Feature Selection (CFS)

CFS selects features based on the ranks attributes according to an empirical evaluation function based on correlations. Subsets made of attribute vectors are evaluated by evaluation function, which are associated with the labels of class, however autonomous among each another. CFS accepts that unrelated structures express a low correspondence with the class and hence they are ought to be overlooked by the procedure. Alternatively, additional features must be studied, as they are typically hugely correlated with one or additional amount of other features.

6) Classification

Two of the prevalent machine-learning classification algorithms namely, LSVM, and RELM are studied in this article. The results acquired through the experiments of these classifiers show that RELM classifier performs better than others respective of the computation time required and accuracy value. Each of the methods is described in brief in the subsections below.

Support Vector Machine Classifier

Linear support vector machine is principally a supervised binary classifier that classifies separable and non-separable data. This type of classification is usually used in the field of neuroimaging and is deliberated as one of the finest machine-learning method in the domain of the neuroscience for past decades. It discovers the best hyperplane to split both classes which has optimum boundary from support vectors for the duration of the training. The classifier decides on the basis of the estimated hyperplane to test the new data points. For the patterns that are linearly separable, LSVM can be used. Alternatively, LSVM is not capable of guaranteeing improved performance in the complex circumstances with the patterns that are not separable. In such circumstances, Kernel trick is used to extend the LSVM. The input arrays of linear SVM are plotted to the space dimensions using the kernels. Both the linear as well as non-linear radial basis function (RBF) kernels are extensively trained using SVM kernels.

Extreme Learning Machine

ELM (Extreme Learning Machine) is single layer feedforward neural networks. This neural network is implemented using Moore-Penrose generalized inverse to set its weights. Thus, this learning algorithm doesn't require iterative gradient-based backpropagation to tune the artificial hidden nodes. Thus this method is considered as effective solution with extremely reduced complexity. ELM with L number of hidden nodes and g(x) as activation function is expressed as $$Y_L(x) = \sum_{i=1}^{L} \beta_i h_i(x) = h(x)\beta_i \qquad \text{[Equation 6]}$$

Where x is an input vector. $h_i(x)$ is the input to output node from hidden node output. $\beta=[\beta_1, \ldots, \beta_2]T$ is the weight matrix of $i^{th}$ node. The input weight $w_i$ and the hidden layer biases $b_i$ are generated randomly before the training samples are acquired. Thus iterative back-propagation to tune these parameters is not needed. Given N training samples $\{(x_j, t_j)\}_{j=1}^{N}$. The objective function of ELM is expressed as, $$\|H(w_1, \ldots w_{\tilde{N}}, b_1, \ldots, b_{\tilde{N}})\hat{\beta} - T\| = \min_{\beta}\|H\hat{\beta} - T\| \qquad \text{[Equation 7]}$$

$$H(w_1, \ldots w_{\tilde{N}}, b_1, \ldots, b_{\tilde{N}}) = \qquad \text{[Equation 8]}$$
$$\begin{bmatrix} g(w_1.x_1+b_1) & \ldots & g(w_L.x_1+b_L) \\ \vdots & \ldots & \vdots \\ g(w_1.x_N+b_1) & \ldots & g(w_L.x_N+b_L) \end{bmatrix},$$
$$\beta = \begin{bmatrix} \beta_1^T \\ \vdots \\ \beta_L^T \end{bmatrix} T = \begin{bmatrix} t_1^T \\ \vdots \\ t_L^T \end{bmatrix}$$

Here H represents the hidden layer output matrix and T represents output label of training data matrix. The output weight matrix $\beta$ is calculated as $$\beta = H^+ T \qquad \text{[Equation 9]}$$

Here, $H^+$ represents the Moore-Penrose generalized inverse of the matrix H. Since ELM learning approach requires no backpropagation, this method is best suited for the binary and multiclass classification of big data and neuroimaging features. However the decrease in computation time comes with the expense of increase in the error in the output, which ultimately decreases the accuracy. Thus, a regularization term is added to improve generalization performance and make the solution more robust. The output weight of the regularized ELM can be expressed as $$\beta = \left(\frac{I}{C} + H^T H\right)^{-1} H^T T \qquad \text{[Equation 10]}$$

<Example 7> Performance Evaluation

We evaluated the performance using the SVM and RELM classifiers for each specific test including the binary and multiclass test. Confusion matrix is constructed to visualize the performance of the binary classifier in a form of a as shown in Table 2. Correct numbers of prediction of classifier are placed on the diagonal of the matrix. These components are further divided into true positive (TP), true negative (TN), which represent correctly identified controls. Similarly, the false positive (FP) and false negative (FN) represent the number of wrongly classified subjects.

TABLE 2

| Accurate | Predicted Class | |
|---|---|---|
| Class | C1 | C2 |
| C1 | TP | FN |
| C2 | FP | TN |

The proportion of subjects which are correctly classified by the classifier is expressed as the accuracy.

$$ACC = \frac{TP + TN}{TP + TN + FP + FN} \qquad \text{[Equation 11]}$$

However, for dataset with unbalanced class distribution accuracy may be a good performance metric. Thus two more performances are used. These metrics are known as sensitivity and specificity are used.

$$SEN = \frac{TP}{TP + FN} \qquad \text{[Equation 12]}$$

$$SPE = \frac{TN}{TN + FP} \qquad \text{[Equation 13]}$$

The sensitivity (SEN) measures the rate of true positives (TP) while the specificity (SPE) measures rate of true negatives (TN).

<Experiment 1> Demographic and Clinical Findings

We did not find a significant group difference in age in AD versus HC, AD versus MCI and MCI versus HC. However significant group difference was found in MMSE (P<0.01) and CDR (P<0.01) in all group combinations. The gender proportion on both AD and HC is male dominant. AD has 54.83% and HC has 45.16% male dominance. Table 1 shows the detailed descriptions and analysis of these variables.

<Experiment 2> Classification Results

We have observed the performance of our proposed algorithm and compared it with that of the RELM classifier and LSVM classifier for respective test comprising the binary classification. The performance shown by the binary classifier is envisaged as a confusion matrix as presented in Table 1. Elements on the diagonal elements of the matrix specify the accurate estimations by the classifier. These elements are further divided as true positive (TP) and true negative (TN), which signifies appropriately recognized controls. Correspondingly, all the erroneously classified matters can be symbolized by false positive (FP) and false negative (FN). We evaluated the feature selection and classification algorithms on data set using a 10-fold cross validation (CV). First, we divided the subjects into 10 equally sized subsets: each of these subsets (folds), containing 10% of the subjects as test set and remaining 90% for training set. Then feature ranking was performed on the training sets. We used different algorithms to rank the features. Linear SVM and RELM classifiers were trained using these top-ranked features. For each training and test we performed separate feature selection to avoid the feature selection bias during 10-fold cross validation. We calculated cross validated average classification accuracy and standard deviation for specific feature using k-top most ranked features, where k ranges from 1 to 50. We repeatedly tested for 5 iterations and plotted the mean accuracy and standard deviation as shown in FIG. 3 for LASSO feature selection and RELM classifier.

Finally, we calculated the mean accuracy and standard deviation of highest ranked features for different feature selection and classification methods as depicted in FIGS. 5-10 and the bold values in each table indicate the maximum value of accuracy, sensitivity and specificity. Maximum and minimum value of accuracy, sensitivity and specificity are calculated amongst corresponding values estimated for highest ranked features as shown in FIG. 3.

FIGS. 5-7 show the binary classification results using RELM classifier with five different feature selections. Results obtained through the feature selection methods are compared in regards to the performance metrics such as accuracy, sensitivity specificity and f-measure. FIG. 5 summarizes the AD versus HC classification. The LASSO feature selection method outperforms all other methods consider with the highest mean accuracy of 87.72%, mean specificity of 90.93% and mean sensitivity of 84.52%. Additionally, the standard deviation of LASSO is 0.4 which is less than less than 1. Similarly, the classification results of AD versus MCI and NC versus MCI using RELM are shown in FIGS. 6, 7. As shown in FIG. 6, the highest mean accuracy is 96.11 (±0.859) for HC against MCI classification and 93.86 (±0.766) for MCI against AD classification. The standard deviation is less than 1 in both mean classifications. Additionally, the F-score is high in all three classifications (0.883 for HC against AD, 0.973 for HC against MCI, 0.968 for AD against MCI) using LASSO feature section method compared to other feature selection methods. The value of standard deviation less than one indicates that the data points of accuracy estimated tend to be close to the mean. Hence from the result it is very evident that the less inflated accuracy can be obtained using LASSO. Similarly, the high F-score indicates precision of classification is high compared to other feature selection methods.

Similarly, the comparison of classification of HC, MCI and AD using LSVM classifier with different feature selection methods are shown in FIG. 8-10. Similar to RELM, the highest performance result in terms of mean accuracy, specificity, sensitivity and F-score was obtained by using LASSO for all three classification tests. As shown in FIG. 8, we obtained the accuracy of 90.63% specificity of 94.315% and sensitivity of 87.95% and F-score of 0.958 for AD against HC. In FIG. 9 the highest mean accuracy, specificity, sensitivity and F-score are obtained as 98.9, 99.68, 98.11, and 0.9856% for HC against MCI classification. Similarly, FIG. 10 shows the classification performance of AD against MCI. The highest mean accuracy, specificity, sensitivity and F-score are 97.81, 97.62, 97.74, and 0.98%.

From all these results, it is clearly evident that the use of LASSO as feature selection method is ideal choice for the classification using RELM and LSVM classifiers for the graph embedded data.

From FIGS. 5-7 the highest classification accuracies of RELM classifier using LASSO feature selection for AD against HC. HC against MCI and MCI against AD are 87.723% (±0.468), 96.11% (±0.859), and 93.86% (±0.766). Similarly, from FIGS. 8-10 the highest classification accuracies of RELM classifier using LASSO feature selection for AD against HC, HC against MCI and MCI against AD are 90.63% (±0.515), 98.91% (±0.456), and 97.80% (±0.9862).

Now, the comparison of performance between two classifiers shows that the SVM can classify the given dataset more accurately with the highest mean accuracy for all three binary classifications. However, the small standard deviation of the classification HC against MCI and MCI against AD suggest that the classification accuracy values are less inflated in RELM as compared to LSVM.

The number of hidden layer nodes influences the performance of the RELM classifier. In our experiment, we found 1000 number of hidden layer generated the best performance in terms of accuracy. Similarly, for SVM we set the default parameter defined for the MATLAB library. We performed the classification by varying different parameters on node2vec graph embedding. FIG. 4 shows the effect of different parameters of node2vec on the performance of RELM classifier. We varied the walk length of node2vec from 10 to 100. In all experiments, increased value of walk length decreases the performance of classifier. For this experiment, we fixed two other parameters, dimension and number of walks to 32 and 200. Similarly, we set the parameters p and q to correspond localized random walks. With the smaller value of p and larger value of q, the random walk is easy to sample to the high-order-order proximity. Thus, we selected p and q randomly and performed graph embedding with p=0.1 and q=1.6.

Discussion

Several studies based on rs-fMRI have been carried out for the classification of AD and MCI from HC subjects. Binary classification in combination of different classifier with different feature measure reported the accuracy ranging from 85 to 95% for AD against HC and 62.90 to 72.58% to and MCI against HC as shown in FIGS. 11, 12. These studies used the same MCI and HC subjects from the ADNI2 cohort. One can clearly notice that the number of subjects directly influences the accuracy. As the number of subjects increase the accuracy is decreased. As reported in previous section the highest accuracy for the classification of AD from is obtained in proposed work is 90.63% using the combination of LASSO and LSVM. If we compare the results for MCI against HC, the results obtained in current study outperform all the state of art methods. However, it is not fair to compare performance with other studies directly because each work employ different datasets, preprocessing pipelines, feature measures, and classifiers. Majority of works including have used subjects less than or nearly equal to 30 in each subject class. The main reason behind small number of dataset is the availability of fMRI data in ADNI2 cohort. All of these studies performed classification and made conclusion. Likewise, we also conducted our study using ADNI2 cohort with nearly equal number of subjects with previous studies and the cross validation was also done using these datasets.

Mild cognitive impairment is a transitional stage between the healthy non dementia and dementia stage[2]. This stage is further divided into early MCI (EMCI) and late MCI (LMCI), according to extent of episodic memory impairment. The risk conversion from MCI to AD is higher in LMCI than in EMCI. In this study, we included only EMCI subjects in MCI group. The MCI converted and non-converted to is classified according to CDR and MMSE score. MCI subjects whose CDR undergoes change from 0.5 to 1 and MMSE score goes below 26 in subsequent visits are considered to have fulfilled the criteria to be MCI converted. In our study majority of subjects fulfill to be non-converted MCI. Only few subjects either have changed CDR score or MMSE score during the visits in the interval of 3, 6, 12, and 18 months. Additionally, none of the MCI subjects are recorded in the list of AD subjects.

Conclusion

It is widely accepted that the early diagnosis of AD and MCI plays an import role to take preventive action and to delay the future progression of AD. Thus the accurate classification task of different stages of AD progression is essential. In this study, we demonstrated graph based features from functional magnetic resonance (fMR) images can be used for the classification of AD and MCI from IC. Additionally, we used multiple feature selection techniques to cope with the smaller number of subjects with larger number of feature representations. The appropriate amount of features is extracted from standard Alzheimer's disease Neuroimaging Initiative cohort that lead to maximal classification accuracies as compared to all other recent researches. Among different feature section methods LASSO together with LSVM on graph based features significantly improved the classification accuracy.

The above description is merely illustrative of the present invention, and those of ordinary skill in the art to which the present invention pertains will be able to make various modifications without departing from the essential characteristics of the present invention. Accordingly, the embodiments disclosed in the present specification are intended to illustrate, not to limit the present invention, and the spirit and scope of the present invention are not limited by these embodiments. The protection scope of the present invention should be construed by the following claims, and all descriptions within the scope equivalent thereto should be construed as being included in the scope of the present invention.

What is claimed is:

1. A method of providing diagnostic information for classifying of Alzheimer's disease progression, including;
    1) extracting a first feature;
    2) constructing a brain network graph using graph theory;
    3) converting the brain network graph to a feature vector using node2vec graph embedding;
    4) selecting a second feature;
    5) classifying Alzheimer's disease progression; and
    6) evaluating the classification result,
    wherein the first feature is extracted from one selected from the group consisting of electroencephalography (EEG), functional magnetic resonance imaging (fMRI), single-photon emission computed tomography (SPECT) and positron emission tomography (PET),
    the graph embedding includes sampling, skip-gram, and computing embedding, and
    the selection is selected from the group consisting of support vector machine-recursive feature elimination (SVM-RFE), least absolute shrinkage and selection operator (LASSO), feature selection with adaptive structure learning (FSASL), local learning and clustering based feature selection (LLCFS) and pairwise correlation based feature selection (CFS).

2. The method of claim 1, wherein the evaluation is verified with one or more selected from the group consisting of accuracy (ACC), sensitivity (SEN), and specificity (SPE).

3. The method of claim 1, wherein the classification uses one or more selected from the group consisting of regularized extreme learning machine (RELM) and linear support vector machine (LSVM).

4. The method of claim 1, wherein Alzheimer's disease progression is one selected from the group consisting of healthy control, mild cognitive impairment and Alzheimer's disease.

* * * * *